United States Patent [19]

Aginsky

[11] 4,091,806
[45] May 30, 1978

[54] INTRAMEDULLARY COMPRESSION NAIL FOR THE TREATMENT OF BONE FRACTURES

[76] Inventor: Jacob Aginsky, 18 Rachael Street, Haifa, Israel

[21] Appl. No.: 759,013

[22] Filed: Jan. 13, 1977

[30] Foreign Application Priority Data

Jan. 13, 1976  Israel .................................. 48826

[51] Int. Cl.² .......................... A61B 17/18; A61F 5/04
[52] U.S. Cl. ............................................. 128/92 BC
[58] Field of Search .............. 128/92 BC, 92 R, 92 B, 128/92 BA, 92 BB

[56] References Cited

U.S. PATENT DOCUMENTS

| | | | |
|---|---|---|---|
| 3,678,925 | 7/1972 | Fischer et al. .................. | 128/92 BB |
| 3,759,257 | 9/1973 | Fisher et al. .................... | 128/92 BC |

FOREIGN PATENT DOCUMENTS

| | | | |
|---|---|---|---|
| 2,063,650 | 6/1972 | Germany ......................... | 128/92 BB |
| 587,915 | 1/1959 | Italy ................................ | 128/92 BA |

OTHER PUBLICATIONS

Vitallium Surgical Appliances (Catalog), Austenal Labs. Inc., Mar. 1948, p. 16, Hip Screws; Lippmann Type, Cat. No. 6404.
"Corkscrew-Bolt For Compression-Fixation of Femoral Neck Fractures", by R. K. Lippmann, Amer. Journal of Surgery, vol. 37, No. 1, Jul. 1937, pp. 79-87.

*Primary Examiner*—Ronald L. Frinks
*Attorney, Agent, or Firm*—Bacon & Thomas

[57] ABSTRACT

A nail for insertion into the medullary cavity of a fractured bone, more especially a thighbone, consists of a hollow outer sheath of a diameter substantially equal to that of the narrowest part of the bone cavity, which sheath is longitudinally slotted at the front end adapted to be driven into the bone as far as the flared part at the far end of the bone cavity, while a short rear portion of the sheath is left to protrude out of the rear end of the bone. A wedge provided with inner screw thread is positioned in the slotted front end during insertion of the nail and is adapted to be pulled deeper into the sheath by the rotation of a screw-threaded bar passing through the hollow sheath, said wedge thus spreading the branches formed by the sheath material left between the slots and bringing them in contact with the solid bone structure.

The protruding rear end of the sheath is screw-threaded on its outside, and a nut can be screwed onto it, pressing a ring or washer against the outer portion of the thighbone, thus compressing the fractured bone portions and keeping them in proper alignment.

4 Claims, 3 Drawing Figures

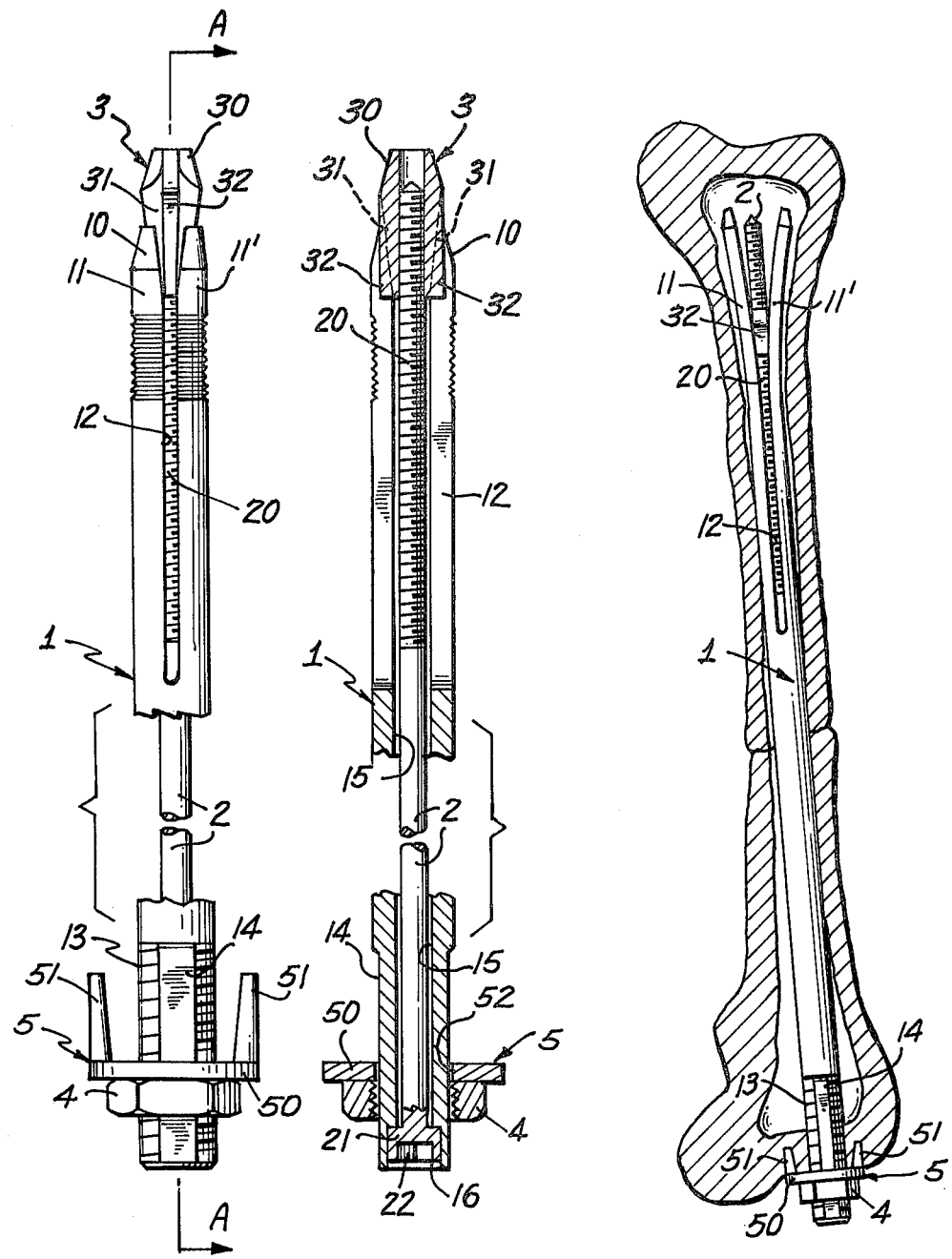

INTRAMEDULLARY COMPRESSION NAIL FOR THE TREATMENT OF BONE FRACTURES

The invention relates to an improved nail for insertion into the medullary cavity of a bone for the purpose of treating fractures.

At present many bone fractures are treated by intramedullary nailing which rejoins and reinforces the broken bone parts and permits the functional rehabilitation of the limb, after a few days' rest.

When this treatment was in its infancy, nails of a non-corrosive material were driven into the bone cavity, the diameter of these nails being commensurate with the narrowest part of the marrow-filled cavity. Necessarily these nails had to be thin throughout and were usually not strong enough to take up the stresses originally carried by the bone, and thus to permit functioning of the limb until it was completely healed. Consequently the limb had to be immobilized for longer periods, which not only rendered the patient unfit for work during that time but also involved the danger of muscle atrophy and other ailments.

In order to hasten the return of mobility of the damaged limb stronger nails had to be used, and it has become modern practice to enlarge the medullary cavity by reaming the bone. The nails that are used when this practice is adopted are of uniform cross-section, throughout their length except for the front tip which is tapered to allow ready progress through the marrow during insertion. Nails of a clover-leaf-shaped cross section are used for large bones, such as e.g. the femur, while V-shape and wire-like forms are employed for bones with a narrow medullary cavity. The cross section of the nail is made compressible and elastic in order to help the nail to cling firmly to both bone fragments; to attain this purpose the "clover-leaf" nail is hollow and longitudinally slotted, which facilitates both a slight longitudinal curvature and the transverse compression of the nail.

The principal drawback of this type of nail is the necessity to enlarge the medullary cavity by reaming, in order to enable a sufficiently strong nail to be inserted. This enlarging of the medullary cavity weakens the shaft of the bone and reduces the blood supply to the fractured ends, thereby impeding the provision of healing factors.

An additional drawback is the fact that the bone fragments are held together exclusively by friction, there being no positive force present to keep the bone fragments aligned and to press the fractured surfaces together.

It is, therefore, the object of the present invention to provide means for pressing the bone fragments against each other, in all those cases in which the shaft has not suffered comminuted fractures. Another object is to provide a mechanically strong nail having a diameter equal to, or smaller than the narrowest cavity passage of the broken bone, thus avoiding detrimental reaming.

The nail — hereinafter termed "compression nail" — according to the invention, serves to prestress the fractured bone in a manner similar to the principle of prestressing known in the construction of concrete beams, whereby all tensile stresses are borne by the steel reinforcement.

The nail is designed with a view to utilizing the fact that the bone cavity flares out towards the two bone ends from the relatively small cross-section in the shaft. The nail has, accordingly, a maximum diameter substantially equal to that of the narrowest part of the bone cavity, thus permitting its unhindered insertion into the bone past the fracture, the rear end of the nail being left to protrude from the bone. The front end of the compression nail is longitudinally slotted so as to form at least two branches, mechanical means being provided for spreading the said branches and bringing them into intimate contact with the solid bone structure in the flared part at the knee — in the case of the femur — of the medullary cavity, thus securely lodging the nail in this part of the bone. The said spreading means is adapted to be operated from the rear, hip-joint end of the nail by longitudinal connecting means passing through the hollow centre of the compression nail to the outside. The protruding rear end of the nail is furthermore provided with means for enabling the nail to rest on, and press against, the platform at the bone end formed by the offset joint ball, thus pressing the two fractured bone parts together and taking up the load exerted on the limb by its movement, by the weight of the body and others.

In a preferred embodiment of the invention the spreading means is wedge-shaped and provided with an inner screw thread in parallel to the nail axis, while the connecting means takes the shape of a screw-threaded bar passing from the said wedge — into which it is screwed — to the rear end of the nail and protruding therefrom, where the said connecting means is provided with means for rotating it so that the wedge may be drawn rearwards into the slotted and branched portion of the compression nail, thus spreading the said branches outwardly.

The means for rotating the nail against the bone end preferably consists of a nut turnably engaged with an outer screw thread cut into the rear end of the nail, which nut is adapted to compress a compression ring against the ledge formed by the offset bone end and thus to pull the lower part of the fractured bone which is held by the branches, against the fractured upper, hip-joint part.

The material of the compression nail, besides being of an anti-corrosive nature, should be highly resilient in order to facilitate the nail's easy withdrawal from the bone after the fracture has healed. To accomplish withdrawal, the spreading means is returned to its original position, occupied during the insertion of the compression nail, thus causing the branches forming the lower, knee-end of the nail once again to come close together by virtue of the nail material's resilience.

In the accompanying drawing which illustrates, by way of example, one embodiment of the invention, FIG. 1 is the side view of a compression nail, FIG. 2 is a section along the line marked A—A on FIG. 1, and FIG. 3 illustrates a fractured thighbone after insertion of a compression nail.

The compression nail illustrated in FIGS. 1 and 2 of the drawing is designed for insertion into the medullary cavity of a fractured thighbone with its front-end pointing towards the knee — at the top of the drawing — while the rear-end of the nail projects out of the bone end for manipulation. The nail comprises a long, cylindrical sheath 1 which is slightly tapered (10) at its front end to facilitate insertion into, and penetration through, the bone marrow. The said front end is divided into two branches, 11 and 11', by a longitudinal slot 12 extending for about half the nail's length. The rear end of the nail sheath is provided with screw thread 13 which is interrupted on opposite sides by two flattened faces 14 machined in parallel to the nail axis, the function of which will be explained further on. A cylindrical bore 15 extends throughout the entire length of the sheath and is slightly enlarged to form a cylindrical recess 16 at the rear end.

A cylindrical threaded bar 2 of a length commensurate with the sheath 1 is movably positioned in the bore 15 thereof, the screw thread 20 extending for about one third of the bar's total length; its rear end forms a collar 21 which in this example is recessed to form a hexagonal socket 22 suitable for the insertion of a so-called "Allen-key".

The threaded front part of the bar engages with an internal screw thread of a wedge 3 which is shaped to form a tapered frontend 30 and, similarly, a tapered rear end 31 (shown in broken lines in FIG. 2). It possesses two lateral ribs 32 on opposite sides which converge towards the rear end and are adapted to engage with the longitudinal slot 12 so as to spread the branches when the wedge is moved to the rear of the sheath. A nut 4 is screwed onto the threaded rear portion of the sheath and is adapted to move a compression ring 5 along the sheath as far as the extent of the screw thread permits. The ring 5 is in the shape of a disc 50 provided with two prongs 51 projecting out of its front face. It is perforated at its centre by an oblong hole 52 which hugs the circumference of the screw thread as well as the flat faces 14, thus preventing relative rotational movement of the sheath and the ring.

FIG. 3 illustrates a section through a bone having a compression nail inserted into its medullary cavity, the nail diameter chosen being slightly smaller than the narrowest portion of the cavity, in order to permit easy movement of the nail during insertion and withdrawal. The branches 11 and 11' are shown to have been spread by the section of the wedge 3 which has moved in a rearward direction. This movement was obtained by rotating the threaded bar 2 by means of an Allen-type spanner inserted into the hexagonal socket 22, thus pulling the wedge rearwards and spreading the branches into intimate contact with the surrounding solid bone material. FIG. 3 also illustrates the compression of the fractured parts by the nut 4 pressing the compression ring 5 against the end portion of the bone, at the same time pressing the prongs into two previously prepared holes in the bone. This arrangement fixes the sheath in a non-rotatable fashion and permits turning of the threaded bar alone.

After the bone has healed the compression nail can be withdrawn, by an operation the mechanical part of which includes:- rotating the threaded bar in reverse direction so as to push the wedge to the front of the sheath which forces the two sheath branches together into their original position by the force of their elasticity; withdrawing the sheath from the medullary cavity by turning the nut 4 as far as thread 13 permits; and finally pulling the nail out completely by applying hammer blows to a hook or the like screwed onto the rear end.

In the foregoing the compression nail was shown and specifically described in respect of a broken femur (thighbone), however it is understood that any other bone fracture may be treated by insertion of a compression nail of the same type, but of other, smaller dimensions.

The threaded bar is of small diameter which permits the bending of the compression nail to the curvature of the medullary cavity before insertion, without impeding the relative movement of the wedge obtained by rotation of the said bar.

The compression nail lends itself to various modifications and alterations to be carried out by a person skilled in the art, however within the spirit of the invention.

It is, for instance, proposed to split the nail sheath into four branches by cutting two perpendicular slots into the front end. Thereby the nail end will be spread into four directions, which should improve the adherence to the flaredout portion of the cavity, with less pressure exerted on the bone.

In case of a comminuted shaft it is proposed to utilize a modified nail designed to support the two bone ends at a distance corresponding to the previous, healthy state. The nail, in this instance, should be provided with a ring 5 that is mechanically connected to a nut 4 in axial direction only, permitting rotation of the nut alone, while the ring is fastened to the bone end, however preventing separation of the nut and the ring while the nut is threaded along the sheath end. In this manner the ring which is connected to the rear bone-end by means of the prongs 51 or by screws, can be drawn outwardly together with the bone end, thus actually increasing the distance between the fractured parts to the state before the fracture.

It is further proposed to provide the branch ends with circumferential narrow serrations which should serve to fasten them intimately to the bone and to prevent relative movement of bone and nail.

I claim:

1. A nail adapted to connect and to compress fractured bone parts, more especially a fractured femur, by its insertion into the medullary cavity of the bone with its front end first and with its rear end protruding out of the drilled bone end, the nail being provided with an expansible portion at its front end to be biased against the bone walls of the flared-out cavity at one end of the bone and with a rear portion provided with means for biasing the protruding end against the outside of the bone at its other end, the nail comprising:

a cylindrical hollow sheath having its front end longitudinally slotted to form at least two spreadable branches and having its rear portion provided with outer screw thread interrupted by at least two flat longitudinal faces adapted to be gripped by a spanner or similar tool, the sheath being further provided with a central cylindrical bore enlarged at its rear end to form a cylindrical recess;

an expansion member adapted to be pulled rearward into the longitudinal slot of the sheath so as to spread said branches, and provided with at least two lateral longitudinal ribs adapted to be moved into the slots between the branches, the expansion member being further provided with a screw-threaded bore extending through its entire length;

a cylindrical bar of a diameter permitting its rotary motion in the bore of the sheath, having its rear end enlarged corresponding to the size of said cylindrical recess in the sheath and having its rear face provided with a recess for engagement with a tool, such as a spanner, for rotating the bar in the sheath, the front portion of the bar being provided with outer screw-thread corresponding to the screw-thread in the expansion member, the latter member being rotatably positioned on the end of the bar;

biasing means in the shape of a compression disc having at least one forwardly protruding prong on its circumference and having a central perforation corresponding in shape to the cross section of the protruding rear portion of the sheath, positioned on said rear portion so as to be movable in axial direction only;

a screw nut positioned on the screw-threaded portion of the sheath to the rear of said compression disc.

2. A nail as defined in claim 1 wherein said expansion member is in the shape of a wedge having a tapered front end and a tapered rear end, the rear end being provided with two opposed lateral ribs converging in width toward the rear of the member.

3. A nail as defined in claim 1 including circumferential serrations on the outside of the sheath branches.

4. A nail as defined in claim 1 wherein the front end of said sheath is tapered.

* * * * *